(12) United States Patent
Kim et al.

(10) Patent No.: US 7,718,695 B2
(45) Date of Patent: May 18, 2010

(54) INCLUSION COMPOUNDS OF FUMAGILLOL DERIVATIVE OR ITS SALT, AND PHARMACEUTICAL COMPOSITIONS COMPRISING THE SAME

(75) Inventors: Jae Hyun Kim, Seoul (KR); Su Kyung Lee, Chungcheongnam-do (KR); Won Kyu Choi, Seoul (KR); Jong Lae Lim, Chungcheongnam-do (KR); Soon Kil Ahn, Seoul (KR); Hee Jong Shin, Kyunggi-do (KR); Chung Il Hong, Chicago, IL (US)

(73) Assignee: Chong Kun Dang Pharmaceutical Corp., Seoul (KR)

(*) Notice: Subject to any disclaimer, the term of this patent is extended or adjusted under 35 U.S.C. 154(b) by 0 days.

(21) Appl. No.: 11/828,025

(22) Filed: Jul. 25, 2007

(65) Prior Publication Data

US 2008/0085929 A1    Apr. 10, 2008

Related U.S. Application Data

(63) Continuation of application No. 10/951,164, filed on Sep. 27, 2004, now abandoned, which is a continuation of application No. PCT/KR02/00583, filed on Apr. 3, 2002.

(30) Foreign Application Priority Data

Mar. 28, 2002    (KR) .................. 10-2002-0016946

(51) Int. Cl.
*A61K 31/336*    (2006.01)
*C07D 303/12*    (2006.01)

(52) U.S. Cl. .................. 514/475; 514/58; 536/103; 549/551; 549/554

(58) Field of Classification Search .............. 514/58, 514/475; 549/551, 554; 536/103
See application file for complete search history.

(56) References Cited

U.S. PATENT DOCUMENTS

| 4,371,673 A | 2/1983 | Pitha | 525/426 |
|---|---|---|---|
| 4,596,795 A | 6/1986 | Pitha | 514/58 |
| 4,727,064 A | 2/1988 | Pitha | 514/58 |
| 5,134,127 A * | 7/1992 | Stella et al. | 514/58 |
| 5,196,406 A * | 3/1993 | Kamei et al. | 514/58 |
| 5,422,363 A | 6/1995 | Yanai et al. | 514/410 |
| 5,840,881 A | 11/1998 | Uda et al. | |
| 6,063,812 A * | 5/2000 | Hong et al. | 514/475 |
| 6,407,079 B1 | 6/2002 | Muller et al. | |

FOREIGN PATENT DOCUMENTS

| EP | 0 415 294 A2 | 3/1991 |
|---|---|---|
| EP | 0519428 | * 12/1992 |
| EP | 0 519 428 B1 | 9/2000 |
| JP | 4297469 A | 10/1992 |
| JP | 6228202 A | 8/1994 |
| WO | WO-99/59986 | 11/1999 |
| WO | WO-00/42849 | 7/2000 |

OTHER PUBLICATIONS

March et al, General, Organic & Biochemistry, Fifth Edition, 1998, pp. 262-263.*
Brewster, et al., "The Potential Use of Cyclodextrins in Parenteral Formulations," Journal of Parenteral Science & Technology 43:5, 231-240 (1989).
Stella, et al., "Cyclodextrins: Their Future in Drug Formulation and Delivery," Pharmaceutical Research 14:5, 556-567 (1997).
Rajewski, et al., "Pharmaceutical Applications of Cyclodextrins. 2. In Vivo Drug Delivery," Journal of Pharmaceutical Sciences 85:11, 1142-1169 (1996).

* cited by examiner

*Primary Examiner*—Shaojia Anna Jiang
*Assistant Examiner*—Ganapathy Krishnan
(74) *Attorney, Agent, or Firm*—Goodwin Procter LLP

(57) ABSTRACT

The present invention relates to an inclusion compound of fumagillol derivative or its salt with hydroxypropyl-β-cyclodextrin or sulfobutylether-7-β-cyclodextrin, and pharmaceutical compositions comprising the same. The inclusion compound according to the present invention has superior water solubility and stability while exhibiting low toxicity, rendering it valuable as an anticancer agent or inhibitor of tumor metastasis.

21 Claims, 2 Drawing Sheets

INCLUSION COMPOUNDS OF FUMAGILLOL DERIVATIVE OR ITS SALT, AND PHARMACEUTICAL COMPOSITIONS COMPRISING THE SAME

CROSS REFERENCE TO RELATED APPLICATIONS

This application is a continuation of U.S. Ser. No. 10/951,164 filed Sep. 27, 2004, now abandoned, which is a continuation of PCT international application no. PCT/KR02/000583 filed Apr. 3, 2002 and published in English as WO 03/082845 on Oct. 9, 2003, which claims the priority of Korean application no. 2002/0016946 filed Mar. 28, 2002.

TECHNICAL FIELD

The present invention relates to an inclusion compound of fumagillol derivative or its salt with hydroxypropyl-β-cyclodextrin or sulfobutylether-7-β-cyclodextrin, and pharmaceutical compositions comprising the same.

BACKGROUND ART

Cyclodextrins are cyclic compounds consisting of glucopyranose units through α-1,4-glycosidic linkages. The exterior surface of the cyclodextrin ring is hydrophilic, whereas the inside cavity thereof exhibits a hydrophobic character. Therefore, it is possible that other molecules referred to as "guest molecule" or part thereof, which are less polar than water (hydrophobic molecules) and have suitable dimensions to be required to fit into the cyclodextrin cavity, are included in the hydrophobic cavity of the cyclodextrin molecule and form inclusion compounds. The pharmaceutical applications with cyclodextrins are disclosed in many articles (*Journal of Parenteral Science & Technology* 43 (5), pp 231-240 (1989) and *Pharmaceutical Research* 14 (5), pp 556-567 (1997)).

Cyclodextrins consisting of 6, 7 or 8 glucopyranose units are generally referred to as α-, β- and γ-cyclodextrin, respectively. Although β-cyclodextrin is the most useful one of the above natural cyclodextrins for pharmaceutical preparations in terms of inclusion capacity and economical efficiency, it is not always ideal for drug formulations due to its relatively low aqueous solubility (1.8 g per 100 ml of water), serious renal toxicity and biological membrane incompatibility after parenteral administration. Therefore, its application is limited to merely food products or oral pharmaceutical preparations.

Recently, a number of chemically modified cyclodextrins such as alkylated-, hydroxyalkylated-, carboxyethylated- and sulfoalkylether-cyclodextrins have been prepared to improve the inclusion capacity and physicochemical properties of natural cyclodextrins.

Among them, as hydroxyalkylated group, Clue alkyl group is preferable, and hydroxymethyl, hydroxyethyl, hydroxypropyl and hydroxybutyl group can be enumerated. In particular, hydroxypropyl group is preferable. In addition, as sulfoalkylated group, $C_{1-6}$ allyl group is preferred, and sulfomethyl, sulfoethyl, sulfopropyl and sulfobutyl group can be enumerated. In particular, sulfobutyl group is preferable. The specific product in the hydroxyalkylated cyclodextrins includes 2-hydroxypropyl-β-cyclodextrin, and the specific product in the sulfoalkylether cyclodextrins includes sulfobutylether-7-β-cyclodextrin. Hydroxypropyl-β-cyclodextrin and sulfobutylether-7-β-cyclodextrin are especially suitable for the parenteral application because of their high water-solubility and minimal-toxicity, which are well disclosed in *Journal of Pharmaceutical Science* 85 (11), pp 1142-1169 (1996).

Further, with regard to cyclodextrin inclusion compounds, U.S. Pat. No. 4,371,673 discloses two types of water-soluble cyclodextrin complexes with retinoid-polymers and complexes of retinoids with ether type derivatives of cyclodextrins. U.S. Pat. No. 4,596,795 discloses results for administering a complex of sex hormone and cyclodextrin derivative via sublingual and buccal route. And U.S. Pat. No. 4,727,064 describes results on the conversion methods of drugs with ready crystallization and low water-solubility into intrinsically amorphous complexes, which have improved pharmaceutical properties by using cyclodextrin derivatives. U.S. Pat. No. 5,134,127 discloses sulfoalkylether cyclodextrin derivatives and their use as solubilizing agents for poorly water-soluble drugs for oral, intranasal or parenteral administration.

Recently, it has been proposed as a promising concept that solid tumor growth beyond a certain size requires newly-formed blood vessels for the transport of nutrients and oxygen, which is called to be angiogenesis-dependent, and it is expected that the inhibition of angiogenesis would provide a powerful and selective therapy for a wide variety of tumors. In particular, fumagillol derivative has been reported to exhibit pharmacological properties as an effective inhibiting agent for tumor-induced neovascularization by European Patent No. 415,294 and U.S. Pat. No. 6,063,812. However, further development of those compounds applicable to the clinical use is hampered considerably by the fact that they are poorly soluble in water and very unstable at room temperature.

It is well known that low drug solubility causes low absorption upon oral administration, precluding parenteral formulations. Furthermore, low stability imposes short shelf-life of products, low-temperature storage requirement and restrictions on mechanical movement, resulting in economical inefficiency and inconvenience.

Preparation studies of fumagillol derivatives are disclosed in several literatures. Solubility improvement of fumagillol derivatives was established in U.S. Pat. No. 5,196,406, but the stabilization of resulting products was not disclosed in the art. Other solubility improvement of fumagillol derivatives was established in European patent No. 519,428 but organic solvents such as ethanol, acetonitrile, isopropyl alcohol and acetone rather than cyclodextrins contributed more to the improved solubility. However, the use of organic solvent potentially may cause the side effects of the therapy. That is, further dilution in a large volume parenteral fluid such as saline or 5% dextrose solution on intravenous or intramuscular administration could lead to life-threatening precipitation followed by phlebitis due to the limited solubility. Also, in the art, stability was not consistent depending on the particular kind of cyclodextrin derivative. The stability of the mixture with maltosyl-β-cyclodextrin was improved, whereas the stability of the mixture with hydroxypropyl-β-cyclodextrin was rather worse than the parent compound alone. In addition, though the formulation with maltosyl-β-cyclodextrin seemed to be stable, maltosyl-β-cyclodextrin has not been yet guaranteed for a parenteral use, and its cost has made its universal use for various formulations economically unfavorable in contrast to hydroxypropyl-β-cyclodextrin that proved to be safe and economical. Also, though a stable composition of fumagillol derivatives was disclosed in U.S. Pat. No. 5,422,363, all excipients, fatty acid esters of glycerin or polyglycerin, used in the formulations are not suitable for the parenteral application.

Therefore, there was a need to convert fumagillol derivatives into a form, which is better soluble and stable, and thus possesses improved pharmaceutical properties.

Concerning the above, the inventors of the present invention developed novel fumagillol derivative and filed (U.S. Pat. No. 6,063,812), and the compounds used in the present invention are identical to the compounds disclosed therein.

The present inventors continued studies to provide fumagillol derivative preparations that can be applicable to parenteral administration such as intravenous or intramuscular injection, or oral administration by ensuring homogeneity, safety, bioavailability and stability under storage at room temperature through increasing solubility of fumagillol derivatives or their salts which were found to be superior as an angiogenesis inhibitor but unstable under storage at room temperature or in aqueous solution. As a result, we discovered that the inclusion compound of fumagillol derivative or its salt with hydroxypropyl-β-cyclodextrin or sulfobutylether-7-β-cyclodextrin is useful as an antitumor agent or antimetastatic agent with superior water-solubility and stability but low irritancy effect, and based on these, completed the present invention.

Therefore, the object of the present invention is to provide inclusion compound of fumagillol derivative or its salt with hydroxypropyl-β-cyclodextrin or sulfobutylether-7-β-cyclodextrin, and pharmaceutical composition comprising the same.

DISCLOSURE OF INVENTION

The present invention relates to the inclusion compound of fumagillol derivative of the following Formula 1 or its salt with hydroxypropyl-β-cyclodextrin or sulfobutylether-7-β-cyclodextrin, and pharmaceutical compositions comprising the same:

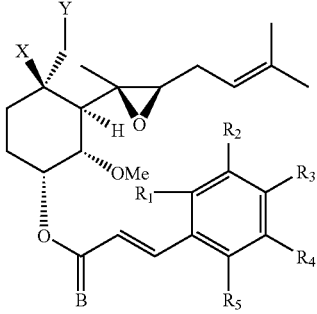

[Formula 1]

Wherein,

X is hydroxy, Y is halogen, or X and Y together forms oxirane ring;

B is O or $H_2$; and $R_1$, $R_2$, $R_3$, $R_4$ and $R_5$ independently represent hydrogen, hydroxy, acetoxy, $C_1$-$C_6$ alkyl, $C_1$-$C_6$ alkoxy, amino, alkylamino, dialkylamino, aminoalkyl, alkylaminoalkyl, dialkylaminoalkyl, aminoalkoxy, alkylaminoalkoxy, dialkylaminoalkoxy, halogen, cyano, trifluoromethyl, nitro, formyl, acetamido, methyleneoxycarboxy, methylenedioxy or ethylenedioxy group, provided that $R_1$, $R_2$, $R_3$, $R_4$ and $R_5$ cannot be hydrogen at the same time.)

Specifically, the inclusion compound of the present invention is characterized in that it includes angiogenesis inhibitor as a main component, in particular fumagillol derivative of said Formula 1 or its salt and as a solubilizing and stabilizing agent, cyclodextrin derivative, in particular hydroxypropyl-β-cyclodextrin or sulfobutylether-7-β-cyclodextrin without addition of any organic solvent.

Fumagillol derivative or its salt of the present invention is preferred to be the following compounds:
O-(4-chlorocinnamoyl)fumagillol;
O-(4-aminocinnamoyl)fumagillol;
O-(4-dimethylaminoethoxycinnamoyl)fumagillol;
O-(4-methoxycinnamoyl)fumagillol;
O-(4-dimethylaminocinnamoyl)fumagillol;
O-(4-hydroxycinnamoyl)fumagillol;
O-(3,4-dimethoxycinnamoyl)fumagillol;
O-(3,4-methylenedioxycinnamoyl)fumagillol;
O-(3,4,5-trimethoxycinnamoyl)fumagillol;
O-(4-nitrocinnamoyl)fumagillol;
O-(3,4-dimethoxy-6-aminocinnamoyl)fumagillol;
O-(4-acetoxy-3,5-dimethoxycinnamoyl)fumagillol;
O-(4-ethylaminocinnamoyl)fumagillol;
O-(4-ethylaminoethoxycinnamoyl)fumagillol;
O-(3-dimethylaminomethyl-4-methoxycinnamoyl)fumagillol;
O-(4-trifluoromethylcinnamoyl)fumagillol;
O-(3,4-dimethoxy-6-nitrocinnamoyl)fumagillol;
O-(4-acetoxycinnamoyl)fumagillol;
O-(4-cyanocinnamoyl)fumagillol;
4-(4-methoxycinnamoyl)oxy-2-(1,2-epoxy-1,5-dimethyl-4-hexenyl)-3-methoxy-1-chloromethyl-1-cyclohexanol;
O-(3,4,5-trimethoxycinnamoyl)fumagillol;
O-(4-dimethylaminocinnamoyl)fumagillol;
O-(3,4,5-trimethoxycinnamoyl)oxy-2-(1,2-epoxy-1,5-dimethyl-4-hexenyl)-3-methoxy-1-chloromethyl-1-cyclohexanol;
O-(4-dimethylaminocinnamoyl)oxy-2-(1,2-epoxy-1,5-dimethyl-4-hexenyl)-3-methoxy-1-chloromethyl-1-cyclohexanol;
O-(3,5-dimethoxy-4-hydroxycinnamoyl)fumagillol; or a salt thereof.

More preferably, the fumagillol derivative or its salt according to the present invention is the following compounds:
4-(4-methoxycinnamoyl)oxy-2-(1,2-epoxy-1,5-dimethyl-4-hexenyl)-3-methoxy-1-chloromethyl-1-cyclohexanol;
O-(4-methoxycinnamoyl)fumagillol;
O-(3,5-dimethoxy-4-hydroxycinnamoyl)fumagillol;
O-(4-dimethylaminoethoxycinnamoyl)fumagillol;
O-(3,4,5-trimethoxycinnamoyl)fumagillol;
O-(3,4-dimethoxy-6-aminocinnamoyl)fumagillol; or a salt thereof.

Further preferably, fumagillol derivative or its salt of the present invention is O-(4-dimethylaminoethoxycinnamoyl)fumagillol or O-(3,4,5-trimethoxycinnamoyl) fumagillol.

In addition, as the fumagillol derivative salt of the present invention, it is preferable to select from a group consisting of salts of fumagillol derivative with hydrochloric acid, bromic acid, sulfuric acid, phosphoric acid, nitric acid, formic acid, acetic acid, trifluoroacetic acid, oxalic acid, fumaric acid, tartaric acid, maleic acid, methanesulfonic acid, benzenesulfonic acid or para-toluenesulfonic acid.

Fumagillol derivative represented with the formula 1 used in the present invention were disclosed in U.S. Pat. No. 6,063,812, and prepared according to the method disclosed therein.

The inclusion compound of the present invention can be prepared by dissolving hydroxypropyl-β-cyclodextrin or sulfobutylether-7-β-cyclodextrin in distilled water, and adding fumagillol derivative or its salt under stirring, or can be prepared by dissolving hydroxypropyl-β-cyclodextrin or sulfobutylether-7-β-cyclodextrin in distilled water, and adding fumagillol derivative or its salt under stirring after adjusting the solution pH in a range of 6-8 with dilute hydrochloric acid or sodium hydroxide solution.

In addition, the inclusion compound of the present invention can be prepared by dissolving hydroxypropyl-β-cyclodextrin or sulfobutylether-7-β-cyclodextrin in buffer solution which pH was pre-adjusted in a range of 6-8 with phosphate buffer, and by adding fumagillol derivative or its salt under stirring.

The produced inclusion compound can be provided as pure product, i.e. in the form of solution or in a solid form via lyophilization, and if necessary, before freeze drying, final solution obtained after shaking can undergo pH adjustment step in the range of 6-8.

The Inclusion compound obtainable according to the present invention can be used as various forms, e.g. solid or solution.

In this invention, it is preferred that the molar ratio of fumagillol derivative or its salt to hydroxypropyl-β-cyclodextrin or sulfobutylether-7-β-cyclodextrin is 1:1 to 1:10, and more preferably, 1:1 to 1:6.

The inclusion compound of fumagillol derivative or its salt according to the present invention has superior solubility and stability compared to other preparations of fumagillol derivative.

As result of solubility evaluation with cosolvents and surfactants, O-(4-dimethylaminoethoxycinnamoyl)fumagillol exhibited the solubility of about 5 mg/ml in aqueous formulations containing a mixture of 10% ethanol and 10% Tween 80® or 10% Cremophor-EL® alone. However, these formulations have a number of disadvantages, which are the inability to guarantee the long-term stability due to facile hydrolysis in solution state, the inability to be buffered due to increased sensitivity to ions resulting in precipitation and further, the toxicity of the surfactants.

In contrast, the inclusion compound of the present invention has been found to have improved solubility over other formulations indicated above. For example, the solubility of O-(4-dimethylaminoethoxycinnamoyl)fumagillol is enhanced from 50 μg/ml in water to about 7 mg/ml in 7 w/v % hydroxypropyl-β-cyclodextrin solution and about 30 mg/ml in 14% w/v hydroxypropyl-β-cyclodextrin solution at pH 6.7, respectively. The solubility of O-(4-dimethylaminoethoxycinnamoyl)fumagillol is about 5.5 mg/ml in 7 w/v % sulfobutylether-7-β-cyclodextrin solution. Thus, depending the pH and the concentration of hydroxypropyl-β-cyclodextrin or sulfobutylether-7-β-cyclodextrin present in solution, the aqueous solubility of O-(4-dimethylaminoethoxycinnamoyl) fumagillol is found to increase by 20-1000 fold.

In addition, the stability of the inclusion compound in the present invention was surprisingly improved at room temperature. The results showed that the degradation rate of O-(4-dimethylaminoethoxycinnamoyl)fumagillol included in hydroxypropyl-β-cyclodextrin was decreased greatly in solid state at room temperature, compared with that of O-(4-dimethylaminoethoxycinnamoyl)fumagillol alone. The preferred inclusion compound in the present invention also suppressed the hydrolysis rate of O-(4-dimethylaminoethoxycinnamoyl)fumagillol in solution.

Therefore, the inclusion compound in the present invention can be applied to the parenteral or oral formulation, since it eliminates the disadvantage of other formulations with cosolvents and surfactants. The preferred inclusion compound in the present invention also overcomes ionic strength effects, which permits the use of buffers to control the pH of solution, and is fully dilutable because of a linear increase in the solubility of the fumagillol derivative as function of hydroxypropyl-β-cyclodextrin or sulfobutylether-β-cyclodextrin concentration. Therefore, it can offer a wide choice of diluents such as electrolytes and non-electrolytes.

The present invention is further characterized by providing pharmaceutical composition comprising the inclusion compound according to the present invention and pharmaceutically acceptable additives.

The pharmaceutically acceptable additives include diluents of pharmaceutically acceptable electrolytes or non-electrolytes, buffers, flavoring agents, binders, thickeners, lubricants, preservatives and the like, and the composition of the present invention can include at least one selected from those ingredients.

Herein, it is preferable that said buffer included in the composition of the present invention is phosphate buffer.

The pharmaceutical formulation can be formulated into oral or parenteral preparation. For parenteral preparation, injection, eye drop, nasal formulation can be enumerated, and preferred injection includes subcutaneous, intravenous, intramuscular, intraarterial and infusion administrations.

Further, the pharmaceutical composition of the present invention can be formulated into the sustained-release dosage form.

The pharmaceutical composition according to the present invention can be used as an anti-tumor agent or a tumor metastasis inhibitor in human beings with tumor, and can also be used for the treatment in warm-blooded animals such as rats, dogs, rabbits, cats and chickens.

BEST MODE FOR CARRYING OUT THE INVENTION

Figure 1:
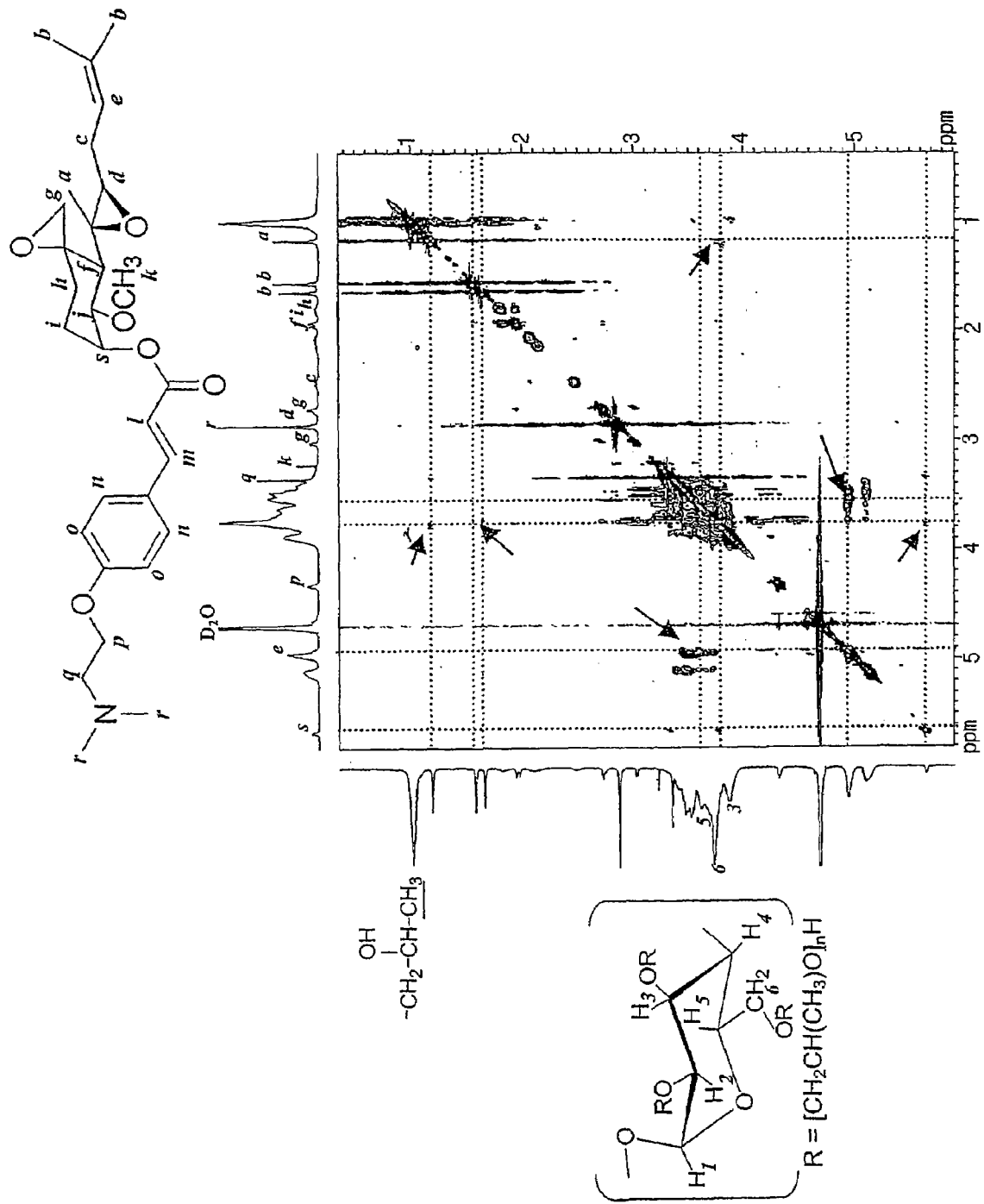
FIG. 1 shows two-dimensional nuclear magnetic resonance spectrum (NOSEY) for the inclusion compound of fumagillol derivative in Example 12.

The following Examples represent preferred embodiments of the present invention. However, the present invention is not limited to the following Examples.

Example 1

O-(4-dimethylaminoethoxycinnamoyl)fumagillol (30 mg) was added to 10.5, 3.5, 7.0, 14.0, 28.0 w/v % hydroxypropyl-β-cyclodextrin solution, respectively, and stirred at 4° C. After 72 hr. the mixture was filtered with 0.2 μm membrabe filter and O-(4-dimethylaminoethoxycinnamoyl)fumagillol in the filtrate was determined by high pressure liquid chromatography (HPLC). The solubility of O-(4-dimethylamino ethoxycinnamoyl)fumagillol as a function of the hydroxypropyl-β-cyclodextrin concentration was represented in Table 1.

TABLE 1

| Concentration of hydroxypropyl-β-cyclodextrin (w/v %) | Solubility (mg/ml) |
|---|---|
| 0 | 0.05 |
| 1.5 | 1.03 |
| 3.5 | 2.93 |

TABLE 1-continued

| Concentration of hydroxypropyl-β-cyclodextrin (w/v %) | Solubility (mg/ml) |
|---|---|
| 7.0 | 6.95 |
| 14.0 | 11.54 |
| 28.0 | 22.64 |

As in apparent from Table 1, the solubility of O-(4-dimethylaminoethoxycinnamoyl)fumagillol was improved when hydroxypropyl-β-cyclodextrin was added to form a complex and when the concentration of hydroxypropyl-β-cyclodextrin was increased.

Example 2

O-(4-dimethylaminoethoxycinnamoyl)fumagillol (30 mg) was added to 1.5, 3.5, 7.0, 14.0, 28.0 w/v % sulfobutylether-7-β-cyclodextrin solution, respectively, and stirred at 4° C. After 72 hr, the mixture was filtered with 0.2 µm membrabe filter and O-(4-dimethylaminoethoxycinnamoyl)fumagillol in the filtrate was determined by high pressure liquid chromatography (HPLC). The solubility of O-(4-dimethylaminoethoxycinnamoyl)fumagillol as a function of the sulfobutylether-7-β-cyclodextrin concentration was represented in Table 2.

TABLE 2

| Concentration of sulfobutylether-7-β-cyclodextrin (w/v %) | Solubility (mg/ml) |
|---|---|
| 0 | 0.05 |
| 1.5 | 0.87 |
| 3.5 | 2.24 |
| 7.0 | 5.42 |
| 14.0 | 10.43 |
| 28.0 | 21.30 |

As in apparent from Table 2, the solubility of O-(4-dimethylaminoethoxycinnamoyl)fumagillol was improved when sulfobutylether-7-β-cyclodextrin was added to form a complex and when the concentration of sulfobutylether-7-β-cyclodextrin was increased.

Example 3

O-(3,4,5-trimethoxycinnamoyl)fumagillol (20 mg) was added to 1.5, 3.5, 7.0, 14.0, 28.0 w/v % hydroxypropyl-β-cyclodextrin solution, respectively, and stirred at 4° C. After 72 hr. the mixture was filtered with 0.2 µm membrabe filter and O-(3,4,5-trimethoxycinnamoyl)fumagillol in the filtrate was determined by high pressure liquid chromatography (HPLC). The solubility of O-(3,4,5-trimethoxycinnamoyl)fumagillol as a function of the hydroxypropyl-β-cyclodextrin concentration was shown in Table 3.

TABLE 3

| Concentration of hydroxypropyl-β-cyclodextrin (w/v %) | Solubility (mg/ml) |
|---|---|
| 0 | 0.002 |
| 1.5 | 0.43 |
| 3.5 | 1.52 |
| 7.0 | 3.54 |
| 14.0 | 6.72 |
| 28.0 | 12.02 |

As in apparent from Table 3, the solubility of O-(3,4,5-trimethoxycinnamoyl)fumagillol was improved when hydroxypropyl-β-cyclodextrin was added to form a complex and when the concentration of hydroxypropyl-β-cyclodextrin was increased.

Example 4

O-(3,4,5-trimethoxycinnamoyl)fumagillol (20 mg) was added to 1.5, 3.5, 7.0, 14.0, 28.0 w/v % sulfobutylether-7-β-cyclodextrin solution, respectively, and stirred at 4° C. After 72 hr. the mixture was filtered with 0.2 µm membrabe filter and O-(3,4,5-trimethoxycinnamoyl)fumagillol in the filtrate was determined by high pressure liquid chromatography (HPLC). The solubility of O-(3,4,5-trimethoxycinnamoyl)fumagillol as a function of the sulfobutylether-7-β-cyclodextrin concentration was shown in Table 4.

TABLE 4

| Concentration of sulfobutylether-7-β-cyclodextrin (w/v %) | Solubility (mg/ml) |
|---|---|
| 0 | 0.002 |
| 1.5 | 0.58 |
| 3.5 | 1.38 |
| 7.0 | 2.75 |
| 14.0 | 5.69 |
| 28.0 | 11.67 |

As in apparent from Table 4, the solubility of O-(3,4,5-trimethoxycinnamoyl) fumagillol was improved when sulfobutylether-β-cyclodextrin was added to form a complex and when the concentration of sulfobutylether-β-cyclodextrin was increased.

Example 5

O-(4-dimethylaminoethoxycinnamoyl)fumagillol (50 mg) was added to phosphate buffer (pH 6.7) containing 1.5, 3.5, 7.0 and 14.0 w/v % hydroxypropyl-β-cyclodextrin, respectively, and stirred at 4° C. After 72 hr, the mixture was filtered with 0.2 µm membrabe filter and O-(4-dimethylaminoethoxycinnamoyl)fumagillol in the filtrate was determined by high pressure liquid chromatography (HPLC). The solubility of O-(4-dimethylaminoethoxycinnamoyl)fumagillol as a function of the hydroxypropyl-β-cyclodextrin concentration was shown in Table 5.

TABLE 5

| Concentration of hydroxypropyl-β-cyclodextrin (w/v %) | Solubility (mg/ml) |
|---|---|
| 0 | 2.38 |
| 1.5 | 4.24 |
| 3.5 | 9.86 |
| 7.0 | 17.59 |
| 14.0 | 32.25 |

As in apparent from Table 5, the solubility of O-(4-dimethylaminoethoxycinnamoyl)fumagillol was improved when hydroxypropyl-β-cyclodextrin was added to form a complex and when the concentration of hydroxypropyl-β-cyclodextrin was increased Example 6

Hydroxypropyl-β-cyclodextrin (13 g) was put to mass flask and 60 ml of distilled water was added and stirred or subjected to sonication at 4° C. until clear solution was obtained. The pH of the solution was adjusted in a range of 6-8 with dilute hydrochloric acid or sodium hydroxide. O-(4-dimethylaminoethoxycinnamoyl)fumagillol (1 g) was added and completely dissolved by stirring at 4° C. If necessary, the pH of the final solution was adjusted between 6-8 with dilute hydrochloric acid or sodium hydroxide and filtered through 0.2 μm membrabe filter and the filtrate was lyophilized.

Example 7

Hydroxypropyl-β-cyclodextrin (13 g) was put to mass flask and 60 ml of distilled water was added and stirred or subjected to sonication at 4° C. until clear solution was obtained. The pH of the solution was adjusted in the range of 6-8 with dilute hydrochloric acid or sodium hydroxide. O-(3,4,5-trimethoxycinnamoyl) fumagillol (1 g) was added and completely dissolved by sting at 4° C. If necessary, the pH of the final solution was adjusted in a range of 6-8 with dilute hydrochloric acid or sodium hydroxide and filtered through 0.2 μm membrabe filter and the filtrate was lyophilized.

Example 8

Potassium phosphate (6.8 g) and hydroxypropyl-β-cyclodextrin (21.67 g) were put to mass flask and 100 ml of distilled water was added and stirred or subjected to sonication at 4° C. until clear solution was obtained. O-(4-dimethylaminoethoxycinnamoyl)fumagillol (1.67 g) was added and completely dissolved by stirring at 4° C. The final solution was filtered through 0.2 μm membrabe filter and the filtrate was lyophilized.

Example 9

According to the same method as in Example 8 except using sulfobutylether-7-β-cyclodextrin instead of hydroxypropyl-β-cyclodextrin, inclusion compound of sulfobutylether-7-β-cyclodextrin with O-(4-dimethylaminoethoxy cinnamoyl)fumagillol was prepared.

Example 10

Potassium phosphate (6.8 g) and hydroxypropyl-β-cyclodextrin (21.67 g) were put to mass flask and 100 ml of distilled water was added and stirred or subjected to sonication at 4° C. until clear solution was obtained. O-(4-dimethylaminoethoxycinnamoyl)fumagillol-oxalate (1.84 g) was added and completely dissolved by stirring at 4° C. The final solution was filtered through 0.2 μm membrabe filter and the filtrate was lyophilized.

Example 11

According to the same method as in Example 10 except using sulfobutylether-7-β-cyclodextrin instead of hydroxypropyl-β-cyclodextrin in Example 10, inclusion compound of O-(4-dimethylamino ethoxycinnamoyl)fumagillol-oxalate with sulfobutylether-7-β-cyclodextrin was prepared.

Example 12

The filtrate obtained in Example 6 was lyophilized. The resulting lyophilized product was dissolved in heavy water ($D_2O$) and analyzed by using two-dimensional $^1$H-NMR (NOESY). The results are shown in FIG. 1. The cross peaks indicate that there are interactions between four protons of O-(4-dimethylaminoethoxycinnamoyl)fumagillol and the protons of the glucose skeleton of hydroxypropyl-β-cyclodextrin. These cross peaks were not observed for the spectrum of O-(4-dimethylaminoethoxycinnamoyl)fumagillol alone. These results indicate that O-(4-dimethylaminoethoxycinnamoyl)fumagillol forms an inclusion compound with hydroxypropyl-β-cyclodextrin.

Example 13

The stability of the lyophilized powders obtained in Example 6 was compared with that of O-(4-dimethylaminoethoxycinnamoyl)fumagillol alone under storage at 25° C. The residual amount of O-(4-dimethylaminoethoxycinnamoyl)fumagillol was determined by HPLC. The results are shown in Table 6.

TABLE 6

|  | Residual amount of O-(4-dimethylaminoethoxycinnamoyl)-fumagillol (%) | | | |
| --- | --- | --- | --- | --- |
|  | after 1 month | after 3 month | after 6 month | after 12 month |
| O-(4-dimethylaminoethoxy-cinnamoyl)fumagillol | 72.8 | 54.3 | — | — |
| Inclusion compound of O-(4-dimethylaminoethoxy-cinnamoyl)fumagillol | 99.3 | 98.7 | 97.5 | 93.6 |

As in apparent from Table 6, the stability of complex of O-(4-dimethylaminoethoxycinnamoyl)fumagillol with hydroxypropyl-β-cyclodextrin was improved as compared to that of O-(4-dimethylaminoethoxycinnamoyl)fumagillol alone.

Example 14

The stability of the lyophilized powders obtained in Example 7 was compared with that of O-(3,4,5-trimethoxycinnamoyl)fumagillol alone at 25° C. The residual amount of O-(3,4,5-trimethoxycinnamoyl)fumagillol was determined by HPLC. The results are shown in Table 7.

TABLE 7

|  | Residual amount of O-(3,4,5-trimethoxycinnamoyl)-fumagillol (%) | | | |
| --- | --- | --- | --- | --- |
|  | after 1 month | after 3 month | after 6 month | after 12 month |
| O-(3,4,5-trimethoxycinna-moyl)fumagillol | 65.3 | — | — | — |
| Inclusion compound of O-(3,4,5-trimethoxycinna-moyl)fumagillol | 99.5 | 97.7 | 94.4 | 93.2 |

As in apparent from Table 7, the stability of complex of O-(3,4,5-trimethoxycinnamoyl)fumagillol with hydroxypropyl-β-cyclodextrin was improved as compared to that of O-(3,4,5-trimethoxycinnamoyl)fumagillol alone.

Example 15

The stability of O-(4-dimethylaminoethoxycinnamoyl)fumagillol was investigated in the presence of various concentrations of hydroxypropyl-β-cyclodextrin in acidic, neutral and basic solutions at 50° C. The residual amount of O-(4-dimethylaminoethoxycinnamoyl)fumagillol in each solution was determined by HPLC. The results are shown in Table 8.

TABLE 8

| Concentration of hydroxypropyl-β- cyclodextrin (w/v %) | Acidic (pH 3.2) | | Neutral (pH 7.2) | | Basic (pH 11.5) | |
|---|---|---|---|---|---|---|
| | $k_{obs}$ $(h^{-1})^a$ | Inhibition ratio (%) | $k_{obs}$ $(h^{-1})$ | Inhibition ratio (%) | $k_{obs}$ $(h^{-1})$, | Inhibition ratio (%) |
| 0 | 0.2042 | — | 0.0162 | — | 0.0918 | — |
| 2 | 0.0976 | 52.20 | 0.0141 | 12.96 | 0.0816 | 5.00 |
| 5 | 0.0848 | 58.47 | 0.0137 | 15.43 | 0.0580 | 16.55 |
| 10 | 0.0754 | 63.08 | 0.0122 | 24.96 | 0.0453 | 22.77 |
| 20 | 0.0665 | 67.43 | 0.0115 | 29.01 | 0.0294 | 30.56 |

$^a k_{obs}$: Hydrolysis Rate Constant

As in apparent from Table 8, hydroxypropyl-β-cyclodextrin suppressed the hydrolysis rate of O-(4-dimethylaminoethoxy cinnamoyl)fumagillol significantly.

Example 16

Pre-prepared tumor mass (Lewis lung carcinoma) of 8 mm³ was subcutaneously implanted into the right axillary region of BDF1 mice (4 weeks). When the tumor size was 100-200 mm³, mice were divided randomly into treatment group and control group. The treatment group was administered subcutaneously with O-(4-ethylaminoethoxycinnamoyl)fumagillol or the complex of O-(4-ethylaminoethoxycinnamoyl)fumagillol with hydroxypropyl-β-cyclodextrin at a dose of 30 mg/kg or 120 mg/kg as O-(4-ethylaminoethoxycinnamoyl)fumagillol every other day for 5 injections, while the control group was given injections of 0.2 ml of phosphate buffered saline. The tumors were weighed on the final day, and tumor volume was calculated using the following equation:

Tumor volume (mm³)=$a \times b^2 \times 0.5$ (a: the longest diameter, b: the shortest diameter)

Inhibition ratio (IR %) of the treatment group relative to the untreated control group was calculated using the following equation:

Inhibition Ratio %=(1−Tumor volume of Treatment group/Tumor volume of Control group)×100

Inhibition Ratio %=(1−Tumor weight of Treatment group/Tumor weight of Control group)×100

The results are shown in Table 9.

TABLE 9

| | Total Dose (mg/kg) | Inhibition Ratio (%), | |
|---|---|---|---|
| | | Tumor Tissue Volume | Tumor Tissue Weight |
| Control Group | 150 | 0 | 0 |
| | 600 | 0 | 0 |
| Group administered with O-(4-dimethyl-aminoethoxycinnamoyl)-fumagillol | 150 | 37.7 | 33.6 |
| | 600 | 63.3 | 71.4 |
| Group administered with inclusion compound of O-(4-dimethylaminoethoxy-cinnamoyl)fumagillol | 150 | 32.2 | 34.7 |
| | 600 | 60.4 | 70.8 |

As in apparent from Table 9, the inclusion compound of O-(4-dimethylaminoethoxycinnamoyl)fumagillol exhibits comparable antitumor activity with O-(4-dimethylaminoethoxycinnamoyl)fumagillol alone.

Example 17

O-(4-dimethylaminoethoxycinnamoyl)fumagillol alone and the complex of O-(4-dimethylaminoethoxycinnamoyl)fumagillol with hydroxypropyl-β-cyclodextrin containing the same amount of O-(4-dimethylaminoethoxycinnamoyl)fumagillol were injected via intravenous route, and blood level of the drug was determined. As test animal, 5 male rats were used per 1 group.

Under light ether anesthesia, the femoral arteries and veins of rats were cannulated with PE-50 polyethylene tubing. After complete recovery from anesthesia, O-(4-dimethylaminoethoxycinnamoyl)fumagillol alone or the complex of O-(4-dimethylaminoethoxycinnamoyl)fumagillol with hydroxypropyl-1,3-cyclodextrin dissolved in phosphate buffered saline (pH 6.2) was administered intravenously to the femoral vein through the catheter at a dose of 20 mg/kg as O-(4-dimethylaminoethoxycinnamoyl)fumagillol, respectively. Blood samples (0.15 ml) were collected via the femoral artery immediately after the dose and at designated time intervals (15, 30, 45, 60, 120, 180 and 240 min). The blood samples were centrifuged immediately and the concentrations of O-(4-di-dimethylaminoethoxycinnamoyl)fumagillol in the plasma were determined by HPLC.

Figure 2:
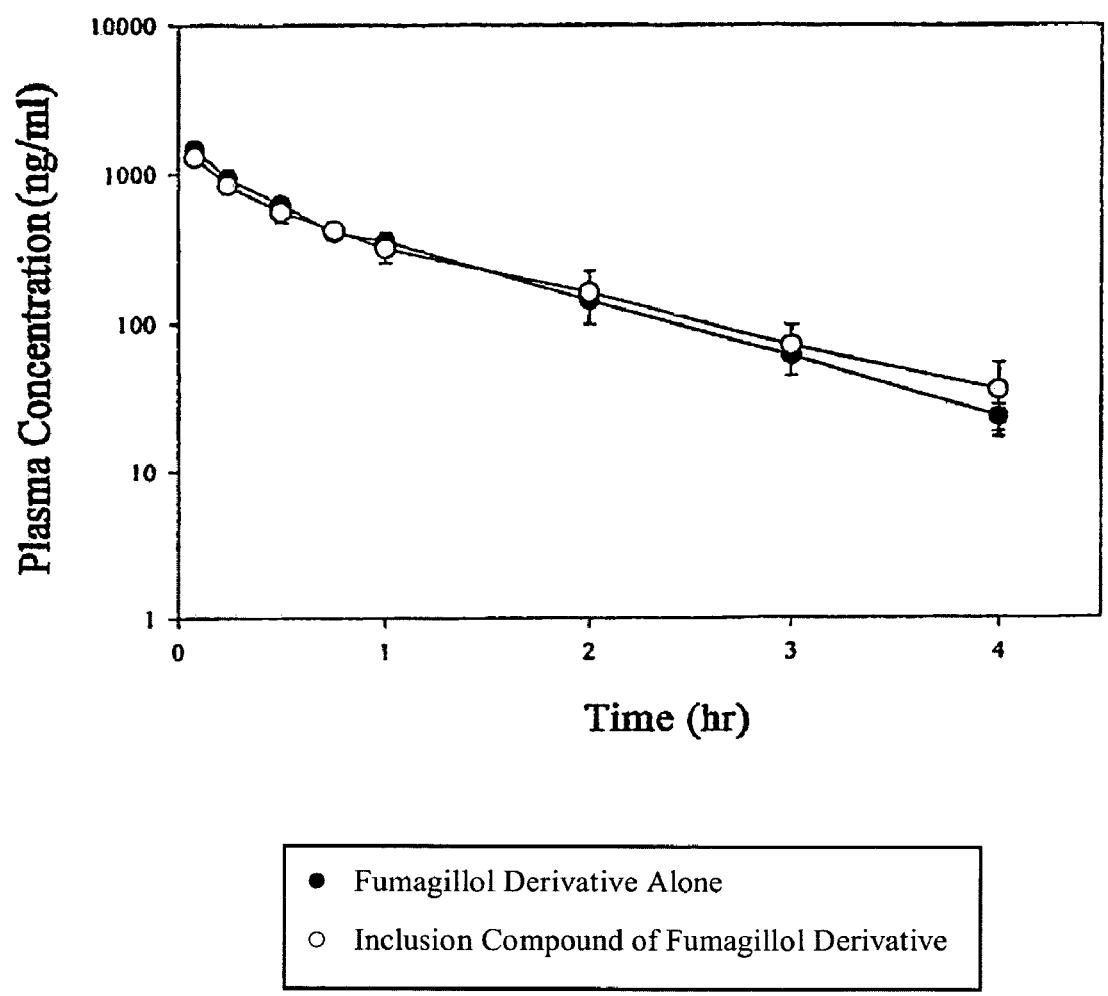
FIG. 2 represents respective plasma concentration-time curve after intravenous administration of fumagillol derivative alone (●) and the inclusion compound of fumagillol derivative (○) in Example 17.

As apparent in FIG. 2, there were no significant differences between the plasma concentrations of O-(4-dimethylaminoethoxycinnamoyl)fumagillol alone and those of the complex of O-(4-dimethylaminoethoxycinnamoyl)fumagillol with hydroxypropyl-β-cyclodextrin. However, it was advantageous that the administration of the complex of O-(4-dimethylaminoethoxycinnamoyl)fumagillol with hydroxypropyl-β-cyclodextrin causes little pain on the injection site in contrast to that of O-(4-dimethylaminoethoxycinnamoyl)fumagillol alone.

INDUSTRIAL APPLICABILITY

The inclusion compound of fumagillol derivative or its salt with hydroxypropyl-β-cyclodextrin or sulfobutylether-7-β-cyclodextrin according to the present invention shows improved water-solubility, superior long-term stability at room temperature and reduced irritancy effect to injection site with unaltered tumor growth inhibitory activity when compared to fumagillol derivative alone, and thus may be useful for the treatment of tumors as an angiogenesis inhibitor.

The invention claimed is:

1. An inclusion compound of a fumagillol derivative or a salt thereof, and hydroxypropyl-β-cyclodextrin or sulfobutylether-7-β-cyclodextrin:

wherein said fumagillol derivative or its salt is O-(4-dimethylaminoethoxycinnamoyl)fumagillol or O-(3,4,5-trimethoxycinnamoyl)fumagillol.

2. The inclusion compound of claim 1 wherein said fumagillol derivative salt is selected from the group consisting of salts of fumagillol derivative with hydrochloric acid, bromic acid, sulfuric acid, phosphoric acid, nitric acid, formic acid, acetic acid, trifluoroacetic acid, oxalic acid, fumaric acid, tartaric acid, maleic acid, methanesulfonic acid, benzenesulfonic acid or para-toluenesulfonic acid.

3. The inclusion compound of claim 1 wherein said inclusion compound is prepared by dissolving hydroxypropyl-β-cyclodextrin or sulfobutylether-7-β-cyclodextrin in distilled water, and adding fumagillol derivative or its salt under stirring.

4. The inclusion compound of claim 1 wherein the inclusion compound is prepared by dissolving hydroxypropyl-β-cyclodextrin or sulfobutylether-7-β-cyclodextrin in buffer solution which pH was pre-adjusted in a range of 6-8 with phosphate, and adding fumagillol derivative or its salt under stirring.

5. The inclusion compound of claim 3 wherein the inclusion compound is obtained by a further lyophilization step of the final solution obtained after stirring.

6. The inclusion compound of claim 3 wherein the molar ratio of fumagillol derivative or its salt to hydroxypropyl-β-cyclodextrin or sulfobutylether-7-β-cyclodextrin is 1:1 to 1:10.

7. A pharmaceutical composition comprising the inclusion compound of claim 1 and a pharmaceutically acceptable additive.

8. The pharmaceutical composition of claim 7 wherein the pharmaceutically acceptable additive is at least one selected from a group consisting of pharmaceutically acceptable diluents, buffers, flavors, binders, thickening agent, lubricants and preservatives.

9. The pharmaceutical composition of claim 8 wherein said buffer is phosphate buffer.

10. The pharmaceutical composition of claim 7 formulated as an oral or parenteral preparation.

11. The pharmaceutical composition of claim 10 wherein said parenteral preparation is for injection.

12. The pharmaceutical composition of claim 7 formulated in sustained-release dosage form.

13. An inclusion compound of O-(4 dimethylaminoethoxycinnamoyl)fumagillol or a salt thereof; and hydroxypropyl-β-cyclodextrin or sulfobutylether-7-β-cyclodextrin.

14. The inclusion compound of claim 13, wherein said compound comprises: O-(4 dimethylaminoethoxycinnamoyl)fumagillol or a salt thereof; and hydroxypropyl-β-cyclodextrin.

15. The inclusion compound of claim 13, wherein the salt is selected from the group consisting of: hydrochloric acid, bromic acid, sulfuric acid, phosphoric acid, nitric acid, formic acid, acetic acid, trifluoroacetic acid, oxalic acid, fumaric acid, tartaric acid, maleic acid, methanesulfonic acid, benzenesulfonic acid or para-toluenesulfonic acid.

16. A lypholized composition comprising the inclusion compound of claim 13.

17. The composition of claim 16, wherein said composition is more stable after 1 month of storage at 25° C., as compared to O-(4 dimethylaminoethoxycinnamoyl)fumagillol or a salt thereof alone.

18. The composition of claim 17, wherein said composition is more stable after 12 months of storage at 25° C., as compared to O-(4 dimethylaminoethoxycinnamoyl)fumagillol or a salt thereof alone.

19. An inclusion compound of O-(3,4,5-trimethoxycinnamoyl)fumagillol; and hydroxypropyl-β-cyclodextrin or sulfobutylether-7-β-cyclodextrin.

20. A lyophilized composition comprising the compound of claim 19.

21. The composition of claim 20, wherein said composition is more stable after 12 months of storage at 25° C., as compared to O-(3,4,5-trimethoxycinnamoyl)fumagillol alone.

* * * * *